United States Patent
Banuelos

(10) Patent No.: US 10,716,910 B2
(45) Date of Patent: Jul. 21, 2020

(54) RESUSCITATOR MOUTH SHIELD ASSEMBLY

(71) Applicant: Jose Banuelos, Los Angeles, CA (US)

(72) Inventor: Jose Banuelos, Los Angeles, CA (US)

( * ) Notice: Subject to any disclaimer, the term of this patent is extended or adjusted under 35 U.S.C. 154(b) by 224 days.

(21) Appl. No.: 16/009,354

(22) Filed: Jun. 15, 2018

(65) Prior Publication Data

US 2019/0381265 A1 Dec. 19, 2019

(51) Int. Cl.
*A61M 16/00* (2006.01)
*A61M 16/08* (2006.01)
*A61B 90/00* (2016.01)

(52) U.S. Cl.
CPC .... *A61M 16/0087* (2013.01); *A61M 16/0084* (2014.02); *A61M 16/0816* (2013.01); *A61B 90/05* (2016.02)

(58) Field of Classification Search
CPC ........ A61M 16/0084; A61M 2025/024; A61M 16/0048; A61M 2039/1027–1038; A61B 90/05; A61B 50/24; A41D 13/11; A41D 13/1107; A41D 13/1138; A41D 13/1184
USPC ........................ 128/205.17, 205.13; 600/119
See application file for complete search history.

(56) References Cited

U.S. PATENT DOCUMENTS

| 4,559,940 | A | 12/1985 | McGinnis |
| D312,330 | S | 11/1990 | Jackson |
| 5,088,485 | A | 2/1992 | Schock |
| 5,782,236 | A * | 7/1998 | Ess ...................... A61M 25/02 128/207.14 |
| 5,813,423 | A | 9/1998 | Kirchgeorg |
| 6,691,703 | B2 | 2/2004 | McKinney |
| 6,763,831 | B2 | 7/2004 | Sniadach |
| 7,077,138 | B2 | 7/2006 | Bateman et al. |
| 7,802,574 | B2 * | 9/2010 | Schultz ............... A61M 1/0047 128/207.14 |
| 9,895,141 | B2 * | 2/2018 | Schultz .................. A61B 13/00 |
| 2003/0145858 | A1 * | 8/2003 | Cardarelli ............... A61F 9/045 128/206.22 |
| 2008/0006270 | A1 * | 1/2008 | Gershman ......... A61M 16/0057 128/203.28 |
| 2011/0226253 | A1 * | 9/2011 | Johnston ............ A41D 13/1123 128/206.19 |
| 2014/0081220 | A1 * | 3/2014 | Connor .................. A61H 37/00 604/289 |

* cited by examiner

*Primary Examiner* — Kendra D Carter
*Assistant Examiner* — Suraj Kandalam

(57) ABSTRACT

A resuscitator mouth shield assembly for protecting a caregiver from bodily fluids during CPR includes a resuscitation bag that has a hose extending toward a face cup. A coupler releasably engages the resuscitation bag and a panel is rotatably coupled to the coupler. The panel is spaced from the resuscitation bag when the coupler is positioned on the resuscitation bag. Moreover, the panel is positioned between a patient's face and a caregiver when the resuscitation bag is positioned on the user's face. In this way the panel inhibits bodily fluids that are expelled from the patient from contacting the caregiver.

5 Claims, 5 Drawing Sheets

RESUSCITATOR MOUTH SHIELD ASSEMBLY

CROSS-REFERENCE TO RELATED APPLICATIONS

Statement Regarding Federally Sponsored Research or Development

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable (f) STATEMENT REGARDING PRIOR DISCLOSURES BY THE INVENTOR OR JOINT INVENTOR Not Applicable

BACKGROUND OF THE INVENTION (1) Field of the Invention (2) Description of Related Art Including Information Disclosed Under 37 CFR 1.97 and 1.98

The disclosure and prior art relates to shield devices and more particularly pertains to a new shield device for protecting a caregiver from bodily fluids during CPR.

BRIEF SUMMARY OF THE INVENTION

An embodiment of the disclosure meets the needs presented above by generally comprising a resuscitation bag that has a hose extending toward a face cup. A coupler releasably engages the resuscitation bag and a panel is rotatably coupled to the coupler. The panel is spaced from the resuscitation bag when the coupler is positioned on the resuscitation bag. Moreover, the panel is positioned between a patient's face and a caregiver when the resuscitation bag is positioned on the user's face. In this way the panel inhibits bodily fluids that are expelled from the patient from contacting the caregiver.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

(i) BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
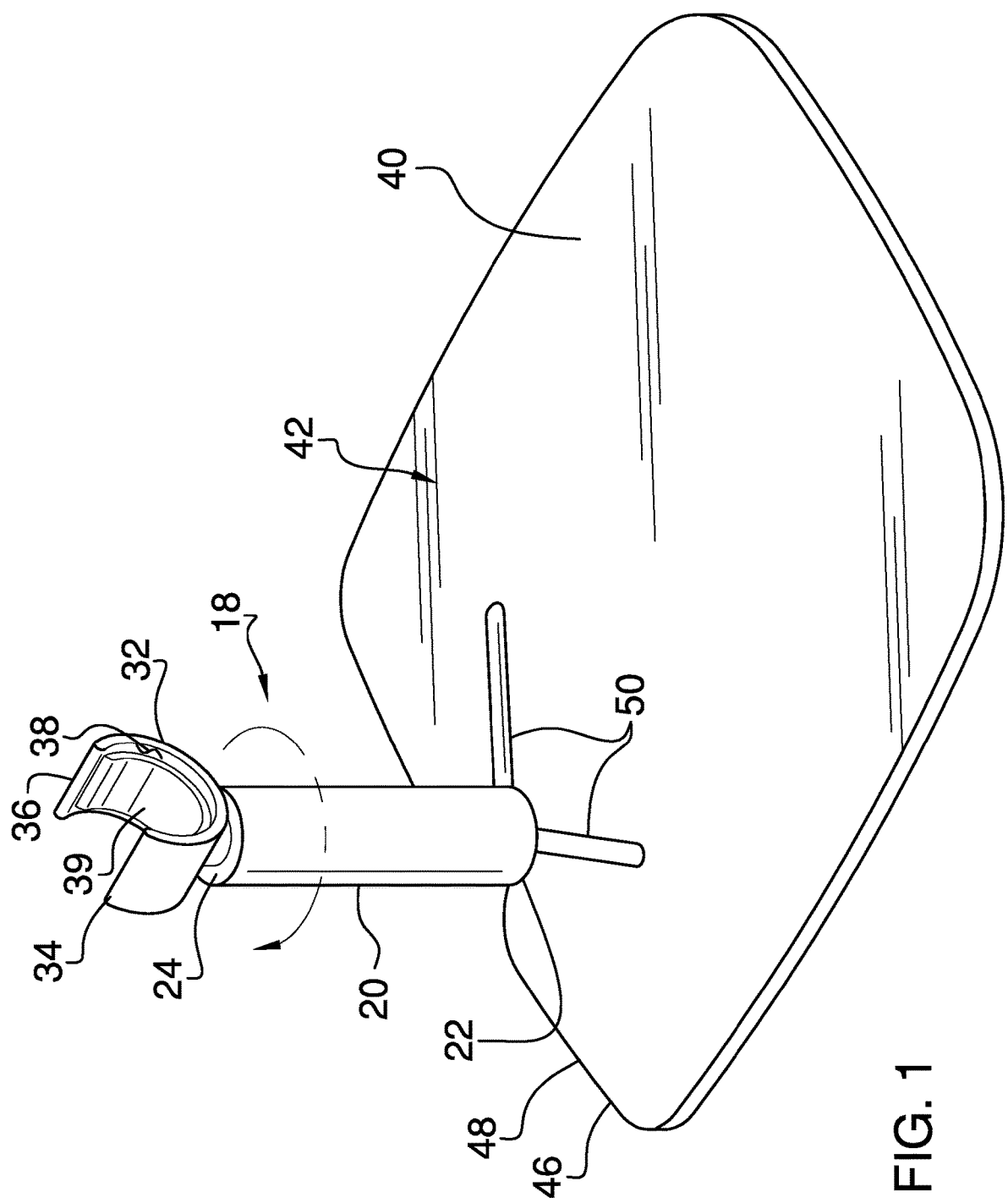
FIG. 1 is a bottom perspective view of panel and a coupler of a resuscitator mouth shield assembly according to an embodiment of the disclosure.
Figure 2:
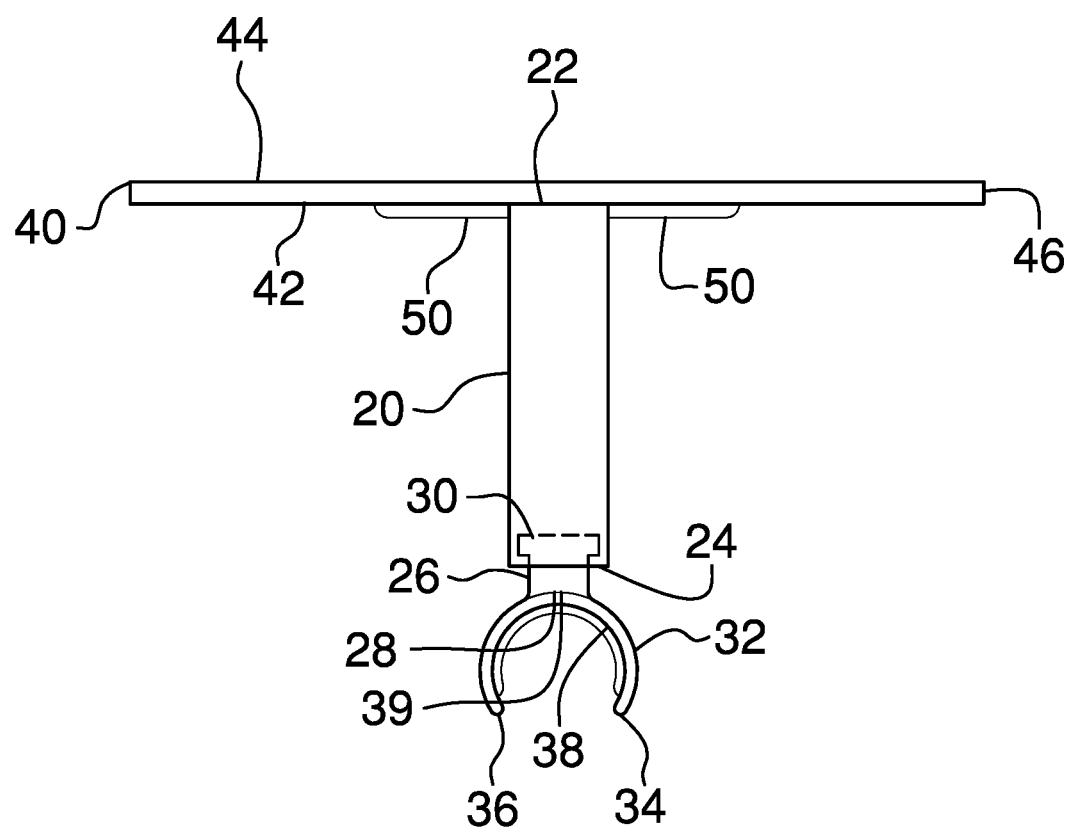
FIG. 2 is a front view of a panel and a coupler of an embodiment of the disclosure.
Figure 3:
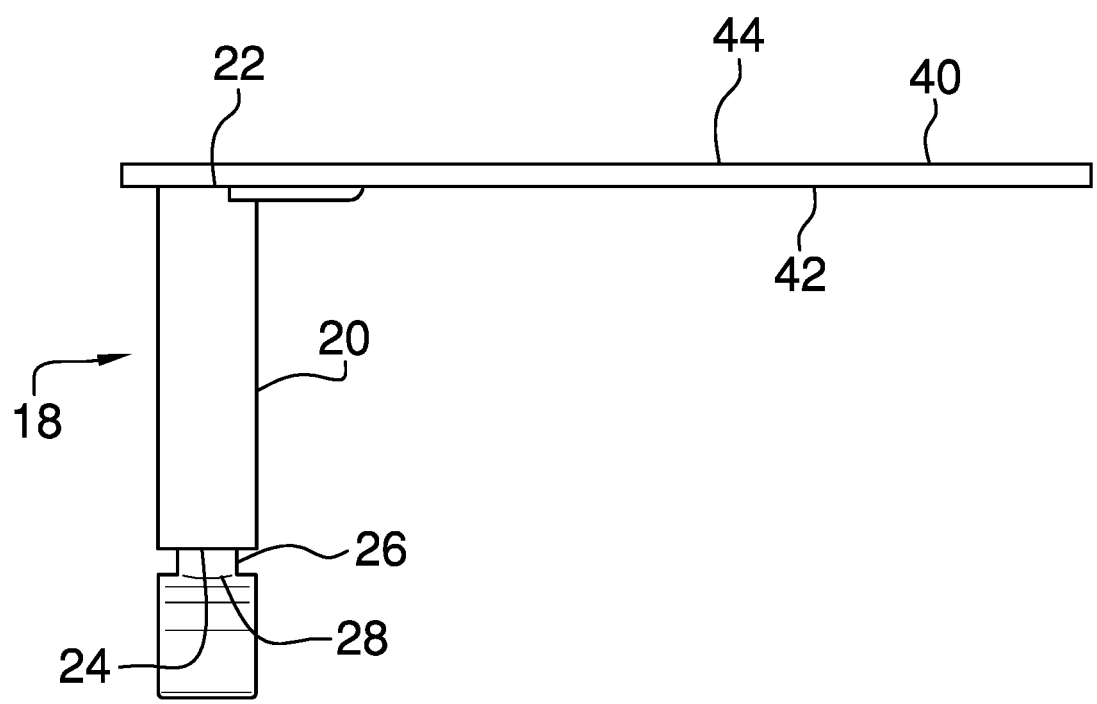
FIG. 3 is a left side view of a panel and a coupler of an embodiment of the disclosure.
Figure 4:
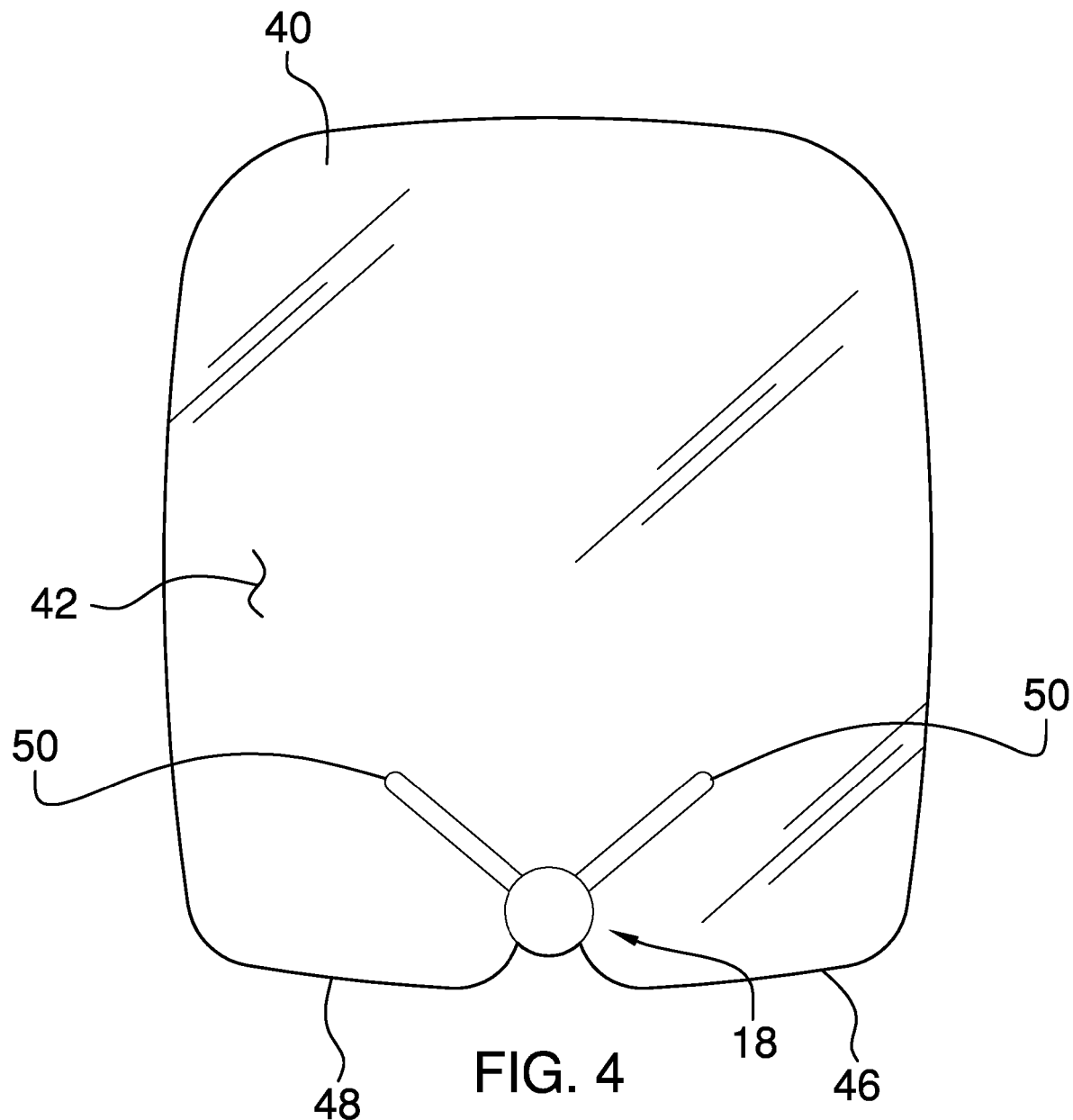
FIG. 4 is a bottom view of a panel and a coupler of an embodiment of the disclosure.
Figure 5:
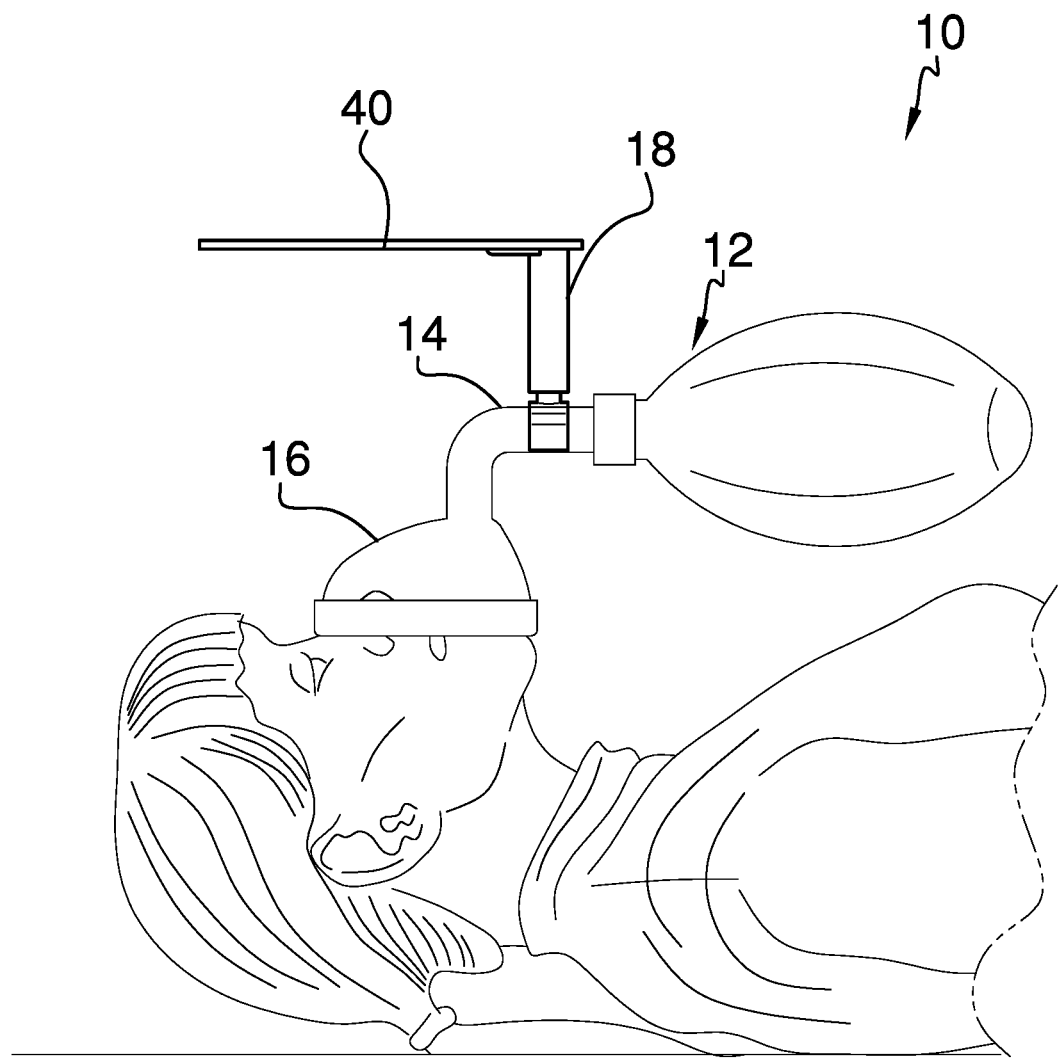
FIG. 5 is a perspective in-use view of an embodiment of the disclosure.

With reference now to the drawings, and in particular to FIGS. 1 through 5 thereof, a new shield device embodying the principles and concepts of an embodiment of the disclosure and generally designated by the reference numeral 10 will be described.

As best illustrated in FIGS. 1 through 5, the resuscitator mouth shield assembly 10 generally comprises a resuscitation bag 12 that has a hose 14 extending toward a face cup 16. The resuscitation bag 12 may be a resuscitation bag commonly employed in a hospital, an ambulance and anywhere else that CPR may be performed. A coupler 18 is provided that releasably engages the hose 14. The coupler 18 comprises a tube 20 that has a first end 22 and a second end 24, and a shaft 26 that is rotatably positioned within the tube 20. The shaft 26 has a distal end 28 with respect to the second end 24 of the tube 20.

A retainer 30 is coupled to the shaft 26 and is positioned within the tube 20. The retainer 30 slidably engages an interior surface of the tube 20 to retain the shaft 26 in the tube 20. The coupler 18 includes a saddle 32 that has a primary end 34, a secondary end 36 and a first surface 38 extending therebetween. The first surface 38 is concavely arcuate between the primary 34 and secondary 36 ends having the primary end 34 being spaced from the secondary end 36. Moreover, the saddle 32 engages the hose 14 having the first surface 38 engaging and conforming to the hose 14. Thus, the tube 20 is rotatably retained on the resuscitation bag 12 having the tube 20 being vertically oriented when the face cup 16 is positioned on a patient's face for performing CPR. A pad 39 is coupled to the first surface 38 of the saddle 32 and the pad 39 frictionally engages the hose 14 for retaining the saddle 32 on the hose 14.

A panel 40 is rotatably coupled to the coupler 18 and the panel 40 is spaced from the face cup 16 when the coupler 18 is positioned on the hose 14. The panel 40 is positioned between the patient's face and a caregiver when the face cup 16 is positioned on the user's face. In this way the panel 40 is positioned to inhibit bodily fluids that are expelled from the patient from contacting the caregiver.

The panel 40 has a first surface 42, a second surface 44 and a peripheral edge 46 extending therebetween, and the peripheral edge 46 has a front side 48. The first surface 42 of the panel 40 has the first end 22 of the tube 20 coupled thereto and the tube 20 is aligned with the front side 48 of the peripheral edge 46 of the panel 40. The front side 48 of the peripheral edge 46 of the panel 40 may curve inwardly to intersect the tube 20. A pair of supports 50 is each coupled to the first surface 42 of the panel 40. Each of the supports 50 engages the tube 20 to retain the tube 20 in a perpendicular orientation with respect to the first surface 42 of the panel 40.

In use, the retainer 30 is engaged to the hose 14 on the resuscitation bag 12 such that the panel 40 is horizontally oriented when the face cup 16 is positioned on the patient's face that is receiving medical treatment. Moreover, the panel 40 is manipulated to be positioned over the patient's face such that the panel 40 blocks vomit or other bodily fluids that are expelled during the administration of CPR from contacting the caregiver. In this way the panel enhances safety and cleanliness of the caregiver during the administration of CPR. Additionally, the panel 40 can be employed during manual ventilation of the patent with an Endrotracheal tube (ET). Thus, the panel 40 blocks bodily fluids in the event that the resuscitation bag 12 becomes disconnected from the ET or if the ET becomes dislodged from the patient's airway. The panel 40 can also be positioned on a ventilator circuit thereby protecting the caregiver from bodily fluids if the ventilator circuit or ET is intentionally or unintentionally disconnected during transportation of the patient.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A resuscitator mouth shield assembly being configured to protect a caregiver from bodily fluids expelled from a patient during CPR, the assembly comprising:
    a resuscitation bag having a hose extending toward a face cup;
    a coupler releasably engaging the hose; and
    a panel, comprising of a saddle, being rotatable with respect to the coupler, the panel being spaced from the resuscitation bag when the coupler is positioned on the resuscitation bag, the panel being positioned between the patient's face and a caregiver when the resuscitation bag is positioned on the user's face wherein the panel is configured to inhibit bodily fluids that are expelled from the patient from contacting the caregiver.

2. The assembly according to claim 1, wherein:
the resuscitation bag has a hose and a face cup; and
the coupler comprises:
    a tube having a first end and a second end;
    a shaft being rotatably positioned within the tube, the shaft having a distal end with respect to the second end of the tube;
    a retainer being coupled to the shaft and being positioned within the tube, the retainer slidably engaging an interior surface of the tube to retain the shaft in the tube; and
    a saddle having a primary end, a secondary end and a first surface extending therebetween, the first surface being concavely arcuate between the primary and secondary ends, the saddle engaging the hose such that the tube is rotatably retained on the resuscitation bag having the tube being vertically oriented when the face cup is positioned on a patient's face for performing CPR.

3. The assembly according to claim 1, wherein:
the coupler includes a tube having a first end; and
the panel has a first surface, a second surface and a peripheral edge extending therebetween, the peripheral edge having a front side, the first surface having the first end of the tube being coupled thereto, the tube being aligned with the front side of the peripheral edge of the panel.

4. The assembly according to claim 3, further comprising a pair of supports, each of the supports being coupled to the first surface of the panel, each of the supports engaging the tube to retain the tube in a perpendicular orientation with respect to the first surface of the panel.

5. A resuscitator mouth shield assembly being configured to protect a caregiver from bodily fluids expelled from a patient during CPR, the assembly comprising:
    a resuscitation bag having a hose extending toward a face cup;
    a coupler releasably engaging the hose, the coupler comprising:
        a tube having a first end and a second end;
        a shaft being rotatably positioned within the tube, the shaft having a distal end with respect to the second end of the tube;
        a retainer being coupled to the shaft and being positioned within the tube, the retainer slidably engaging an interior surface of the tube to retain the shaft in the tube; and
        a saddle having a primary end, a secondary end and a first surface extending therebetween, the first surface being concavely arcuate between the primary and secondary ends, the saddle engaging the hose such that the tube is rotatably retained on the resuscitation bag having the tube being vertically oriented when the face cup is positioned on a patient's face for performing CPR;
    a panel, comprising of a saddle, being rotatable with respect to the coupler, the panel being spaced from the face cup when the coupler is positioned on the hose, the panel being positioned between the patient's face and a caregiver when the face cup is positioned on the user's face wherein the panel is configured to inhibit bodily fluids that are expelled from the patient from contacting the caregiver, the panel having a first surface, a second surface and a peripheral edge extending therebetween, the peripheral edge having a front side, the first surface having the first end of the tube being coupled thereto, the tube being aligned with the front side of the peripheral edge of the panel; and
    a pair of supports, each of the supports being coupled to the first surface of the panel, each of the supports engaging the tube to retain the tube in a perpendicular orientation with respect to the first surface of the panel.

* * * * *